United States Patent [19]

Edward, Jr.

[11] 4,328,702
[45] May 11, 1982

[54] OPERATING CAM STOP MEANS FOR HARDNESS TESTER

[76] Inventor: Robert M. Edward, Jr., 18 Kittiwake Ct., The Woodlands, Tex. 77380

[21] Appl. No.: 167,652

[22] Filed: Jul. 11, 1980

[51] Int. Cl.³ .............................................. G01N 3/44
[52] U.S. Cl. ....................................................... 73/83
[58] Field of Search ...................... 73/81, 83; 33/169 F

[56] References Cited

U.S. PATENT DOCUMENTS 2,938,377  5/1960  Sklar ........................................ 73/83
3,182,491  5/1965  Tschirf et al. ........................... 73/81

*Primary Examiner*—Daniel M. Yasich
*Attorney, Agent, or Firm*—Bill B. Berryhill

[57] ABSTRACT

An operating cam for use with a hardness tester may comprise: first and second cylindrical journal portions for respective disposition with first and second cylindrical holes provided through a housing of the hardness tester; a substantially cylindrical cam portion of smaller diameter between the journal portions and the axis of which is eccentric to the axis of the journal portion; an end portion adjacent the second journal portion having a common axis therewith and engageable for rotating the cam member about the common axis between no load, minor load and major load positions; and stop portions adjacent the end portion engageable with corresponding stop portions on the tester housing for limiting rotation of the operating cam between the no load and major load positions.

9 Claims, 6 Drawing Figures

OPERATING CAM STOP MEANS FOR HARDNESS TESTER

BACKGROUND OF THE INVENTION

1. Field of the Invention

The present invention pertains to hardness testing apparatus. Specifically, it pertains to hardness testing apparatus of the type having a load cell by which predetermined forces can be transferred to a penetrator for measuring hardness properties of materials contacted thereby in response to loads applied through the load cell. Specifically, the invention pertains to operating cams for use with load cell type hardness testers and by which no load, minor load and major load forces, to be applied to the penetrator, are controlled.

2. Brief Description of the Prior Art

Load cell type hardness testers conventionally comprise a housing in which is carried a load cell having major and minor load springs therein. The tester includes a penetrator and a plunger rod by which the load forces of the load cell are transferred to the penetrator. An operating cam is normally provided which in certain positions prevents all or part of the load forces of the load cell from being transferred to the penetrator. The operating cam is normally provided with a handle, rotation of which allows predetermined no load, minor load or major load forces to be applied to the penetrator to indent the material being tested. Depending upon the load transferred from the load cell, the plunger rod and penetrator respond in a predetermined fashion to the indentation of the penetrator in the material being tested. A dial gauge is attached to the tester for engagement with the opposite end of the plunger rod, measuring the response thereof, to determine the hardness of the material being tested.

In hardness testers of the prior art, the operating cam is provided with first and second cylindrical journal portions for disposition within first and second cylindrical holes of the tester and an intervening cylindrical cam portion of a smaller diameter which is eccentric to the axis of the journal portions. One end of the operating cam is provided with a handle or some other means of rotating the cam and the opposite end of the operating cam is provided with a stop member, usually in the form of a pin member which extends from the first cylindrical journal portion. The pin member engages corresponding stop shoulders on the housing of the tester in the no load and major load positions. However, this arrangement creates certain problems.

Due to the relatively large torque which may be applied to the stop pin, the stop pin is frequently sheared off. This is due to the relatively large ratio between the radius at which the operating force is applied to the handle and the relatively small radius of the operating cam journal at which the stop pin is disposed. In addition, the stop pin is usually small in diameter due to the fact that holes for larger stop pins would weaken the operating cam journal. When a stop pin is sheared it must be replaced, sometimes requiring disassembly of the tester.

Another problem with operating cams of the prior art, as just described, is the distortion of the eccentric cam portion. Since it is of smaller diameter than the journal portions of the operating cam and since the stop pin is at an end of the operating cam opposite the handle, the eccentric cam portion must absorb and transfer the torque created by the force applied to the operating handle with the pin in either the no load or major load stop positions. Consequently, the intermediate eccentric cam portion may be twisted or distorted so that an improper load is transferred to the tester penetrator, resulting in inaccurate measurements. Furthermore, if too much torque is applied, it may even result in twisting the operating cam in two.

Thus, it is seen that the operating cam of load cell type hardness testers of the prior art are high maintenance items. Not only does such maintenance result in increased repair costs but it also results in prolonged testing time.

SUMMARY OF THE INVENTION

The operating cam of the present invention, like those of the prior art, is provided with first and second cylindrical journal portions for disposition within corresponding first and second cylindrical holes of the tester housing. Likewise, an intermediate smaller diameter eccentric cam portion is provided between the journal portions. An end portion is provided adjacent the second journal portion having a common axis therewith, and having means thereon for rotating the cam member about the common axis between no load, minor load and major load positions.

Also as in prior art designs, stop means are provided on the operating cam for engagement with corresponding stop means on the housing to limit rotation of the operating cam between no load and major load positions. However, unlike prior art designs, the stop means of the operating cam of the present invention is provided between the second journal portion and the operating end portion. In addition, the stop means is in the form of a radial rib providing greater strength and resistance against shearing than the pin type stop members of the prior art. Furthermore, the stop portion is located on a larger diameter portion of the operating cam so that the force created by torque applied to the handle or operating end portion is less than that created in the prior art version. Still further, since the stop means is between the second journal portion and the operating end portion of the operating cam, no torque at all is applied to the intermediate smaller diameter cam portion, eliminating distortion and breakage problems of the prior art.

Thus, the operating cam of the present invention provides more accurate operation of the tester with which it is used and essentially eliminates any breakage problems associated with the stop pins of the prior art. The result is a more accurate and dependable operating cam with less repair time and less operating downtime. Other objects and advantages of the present invention will be apparent from reading the specification which follows in conjunction with the accompanying drawings.

DESCRIPTION OF PRIOR ART

Figure 1:
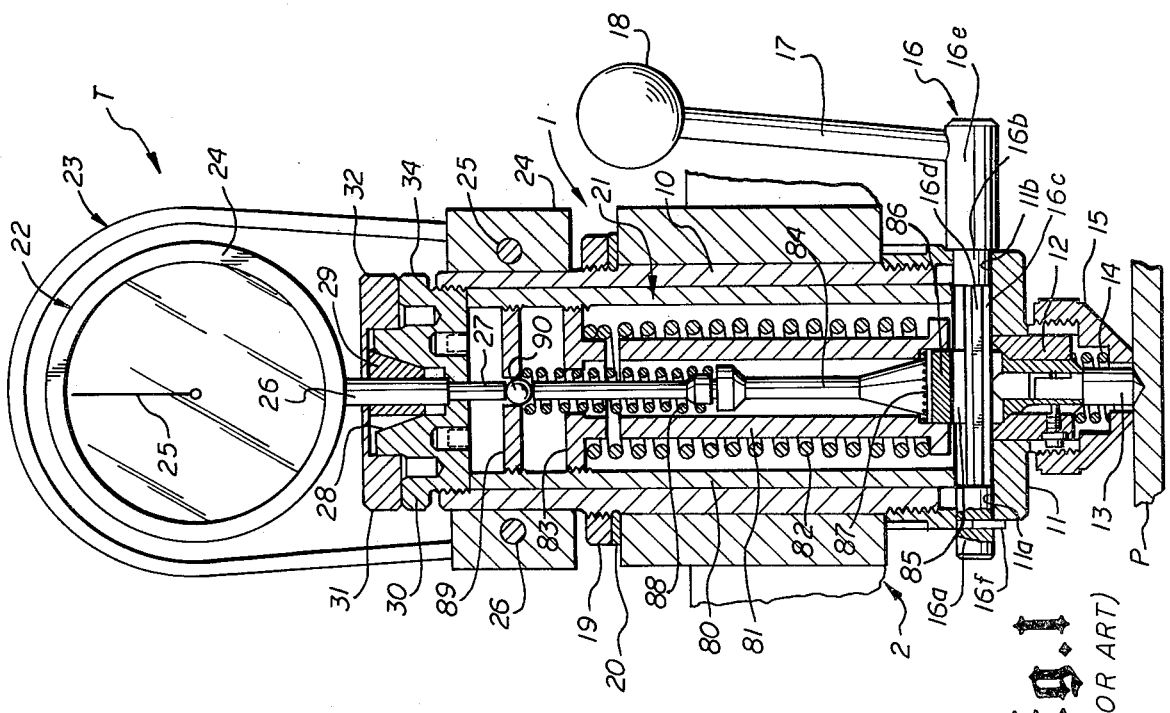
FIG. 1 is an elevation view, partially in section, of a hardness tester illustrating the operation thereof and the use of an operating cam according to prior art.

Referring first to FIG. 1, there is shown a hardness tester T affixed against a metallic plate P, or other material, for testing the hardness thereof. The tester T includes a head unit 1 which is carried in an attachment assembly 2 by which the tester T is affixed or attached next to the plate P. The attachment assembly may be any one of several kinds conventionally available. Since such attachment assemblies are known and form no part of the present invention, it will not be further described hereafter. In fact, in the drawings, most of the mounting assembly 2 has been broken away so as not to interfere with a description of the other tester components.

The head unit 1 of the tester has a tubular housing 10, closed at the lower end thereof by a threaded lower cap or closure member 11 through which is an aperture for receiving a seat member 12 and a reciprocating diamond penetrator 13. A spring 14 seats in the penetrator cap and creates a force against the seat 12. The spring 14 is held in place by a penetrator cap 15. The penetrator cap 15 rests against the plate P or other material being tested.

Extending through the lower cap 11 is an operating cam 16 according to an embodiment of the prior art. As shown, operating cam 16 includes first and second cylindrical journal portions 16a and 16b, respectively, for disposition within first and second cylindrical holes 11a and 11b, respectively, of the lower cap 11. Intermediate the first and second cylindrical journal portions 16a and 16b is a substantially cylindrical cam portion 16c of smaller diameter. The axis of the cylindrical cam portion 16c is eccentrically located relative to the axis of the journal portions 16a and 16b. It will also be noted that a longitudinal flat surface 16d is provided along outside of the eccentric cam portion 16c.

Adjacent the second journal portion 16b is a larger diameter end portion 16e from which an operating handle 17 and knob 18 extend in a generally radial fashion. Radially extending from a hole in the first journal portion 16a is a stop pin 16f, the purpose of which will be more fully explained hereafter. For present purposes, it is sufficient to note that the operating knob 18 of handle 17 may be manually gripped and manipulated so as to rotate the operating cam 16 about the axis of journal portions 16a and 16b, through approximately 180°, between no load, minor load and major load positions, to be more fully understood hereafter.

It will be noted that tubular housing 10 of the tester 10 is received in the bore of the mounting assembly 2 and affixed thereto, the mounting assembly 2 being held between the shoulders of lower cap 11 and a locknut and washer 19 and 20, respectively. Of course, various types of mounting assemblies can be utilized with such a tester unit.

The tester housing 10 receives a load cell 21, the lower end of which is shown adjacent the operating cam 16. Load cells 21 can be removed for repair and replacement by a different load cell. Although load cells may be made in different ways, the one illustrated has a tubular housing 80 in which is centrally disposed a tubular spring mandrel 81, a major load spring 82 and load spring adjusting nut 83.

Centrally disposed in the bore of tubular spring mandrel 1 is a plunger rod 84 in the lower end of which the penetrator 13 is received. It will be noted that a horizontal hole 85 is provided in the lower enlarged portion 86 of the plunger rod 84. It will also be noted that the operating cam 16 extends through this hole 85 perpendicularly to the axis of the plunger rod 84. An upper shoulder of the enlarged portion 86 is provided with a thrust bearing 87 against which the major load spring mandrel 81 rests, and by which the force of major load spring 82 may be transferred to the penetrator 13. Bearing against a shoulder on the upper end of plunger rod 84 is a minor load spring 88. The upper end of the minor load spring 88 bears against an adjustment nut 89. The upper end of plunger rod 84 terminates in a ball portion 90.

Attached at the upper end of the tester housing 10 is a dial gauge 22 and a dial gauge cover or protector 23. The cover or protector 23 can be attached to the tester housing 10 in any suitable fashion. In the embodiment shown, such attachment is provided by a split collar 24 and lock screws 25 and 26.

The dial gauge 22 includes a housing 24 in which is carried an operating mechanism (not shown). Also included is a dial indicator 25. At the base of the dial gauge 22 is a fixed stem 26 through which extends a reciprocating plunger 27. The plunger 27 is connected to the operating mechanism of the dial gauge 22 and movement of the plunger 27 effects movement of the dial indicator 25 in a conventional manner.

It will be noted that the end of the plunger 27 engages the ball portion 90 of the plunger rod 84. To provide for such engagement, mounting apparatus is provided which includes a cap 34 threadedly attached to the tester housing 10. The cap 34 is provided with an aperture in which the stem 26 and plunger 27 are disposed for engagement of the plunger 27 with the plunger rod ball 90. The aperture flares upwardly and outwardly to form a frusto-conical surface 28 for receiving a frusto-conical collet 29. The upper portion of the lock cap 34 is threaded at 30 for engagement by corresponding internal threads of a lock nut 31. It will be noted that the lock nut 31 also has a central aperture and is counterbored so as to provide an end portion 32 which engages the upper surface of collet 29.

Now operation of the tester T will be explained. In FIG. 1, the tester is shown in the major load position. The major load position is assumed when the disposition of the cam portion 16c is at its lowermost limit. In this position, the operating cam does not interfere with the major load spring mandrel 81 or the plunger rod 84, allowing the major load spring 82 and minor load spring 88 to apply maximum force to the plunger rod 84 and consequently to the penetrator 13. If the operating cam 16 were rotated in a clockwise direction, as viewed from the righthand side of the drawings, approximately 90°, the cam portion 16c would rise to a position in which the flat surface 16d provided longitudinally thereon would engage the lower load spring mandrel 81, preventing the force of major load spring 82 from being transferred to the penetrator 13 via bearings 87. However, nothing would prevent the force of minor load spring 88 from being transferred to the penetrator 13 via plunger rod 84. Thus, in this "minor load" position, only the force of minor load 88 would be transferred to the penetrator 13.

If the operating cam 16 were further rotated, in a clockwise direction, approximately 90°, the eccentrically offset cam portion 16c would be at its highest position engaging both the bottom of major load spring mandrel 81 and the enlarged portion 86 of the plunger rod 84 at the upper confines of horizontal hole 84 therethrough. In this, no load position, both the force of the major load spring 81 and the minor load spring 88 would be prevented from being transferred to the penetrator 13.

In fact, in operation, the operating cam 16 would be first placed in the no load position just described. Then it would be rotated counterclockwise 90° to the minor load position where a small amount of indentation of the plate P by the penetrator 13 would take place. A first or minor load reading of the dial gauge 22 would be made at this point. Then, the operating cam 16 would be further rotated in the counterclockwise direction 90° to the major load position of FIG. 1, in which the force of both the major load spring 81 and the minor load spring 88 would be transferred to the penetrator 13. A reading of the dial gauge 22 would be made at this position so that the increased indentation between the minor and major load positions could be determined. The difference between these readings would indicate the hardness of the plate P.

At the major and no load positions, the stop pin 16f would engage corresponding stop shoulders (not shown) on the closure cap 11, preventing the cam member 16 from being rotated past these limits. Engagement of the stop pin 16f with these stop shoulders would also indicate to the operator that the no load and major load positions were properly assumed. The operator would know that the minor load position, intermediate the major and no load positions, was assumed by feeling the engagement of the flat surface 16d with the enlarged portion 86 of the plunger rod.

It will again be noted that in this arrangement of the prior art, the torque created by the force applied to the handle 17 via knob 18 would be transferred to the pin 16f. If too much force were applied to the handle 17 the pin 16f might be sheared, creating a repair or replacement problem. It will also be noted that if too much force were applied to the handle 17, the relatively small diameter of the intermediate cam portion 16c might be distorted, causing an inaccurate reading on the dial gauge 22. It is such problems that the operating cam of the present invention, to be described hereafter, eliminates.

DESCRIPTION OF A PREFERRED EMBODIMENT

Figure 2:
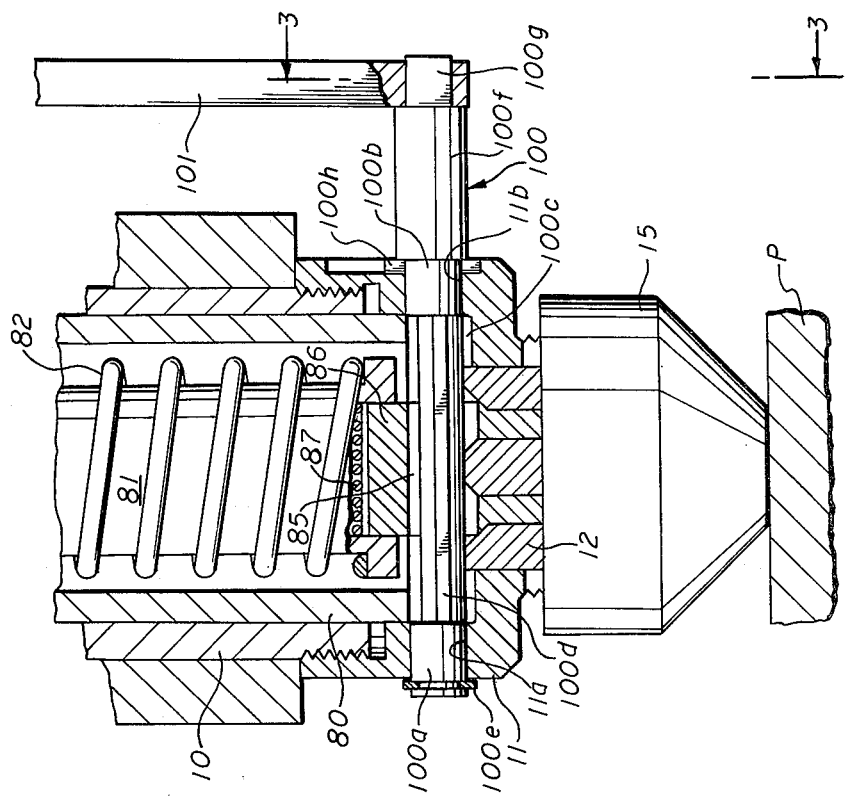
FIG. 2 is an elevation view, partially in section, of the lower portion of a hardness tester such as the one shown in FIG. 1, but utilizing an operating cam according to a preferred embodiment of the present invention.
Figure 3:
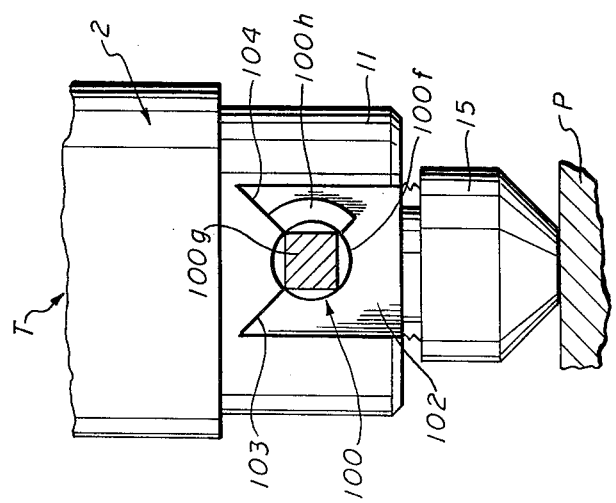
FIG. 3 is an elevation view, similar to FIG. 2, but viewed in the direction indicated by lines 3—3 in FIG. 2.

Referring now to FIGS. 2 and 3, the lower portion of the tester T is again shown. However, instead of the operating cam 16 of the prior art, as previously described with reference to FIG. 1, tester T utilizes an operating cam 100 of a new and improved design according to a preferred embodiment of the present invention. All other components of the tester T shown in FIGS. 2 and 3 are substantially identical to the ones shown in FIG. 1 and the same reference numbers therefor will be used. Like in the prior art embodiment of FIG. 1, FIGS. 2 and 3 represent the operating cam 100 in the major load position.

Like in the prior art embodiment, the operating cam 100 of the present invention includes first and second cylindrical journal portions 100a and 100b, respectively, for disposition within the first and second cylindrical holes 11a and 11b of lower cap 11. Intermediate the first and second cylindrical journal portions 100a and 100b is a substantially cylindrical cam portion 100c of smaller diameter. The axis of the cylindrical cam portion 100c is eccentrically located relative to the axis of journal portions 100a and 100b. The smaller diameter cylindrical cam portion 100c is also provided with a longitudinal flat surface 100d. The first journal portion 100a is provided with a groove in which may be placed a snap ring 100e to prevent displacement of the cam member 100 in a direction to the right as viewed in FIG. 2.

Adjacent the second journal portion 100b is a larger diameter end portion 100f which has a common axis with journal portions 100a and 100b. The end of the larger diameter end portion 100f is provided with a handle engaging extension 100g for receiving a radially extending handle 101.

It will also be noted, particularly with reference to FIG. 3, that at the junction of journal portion 100b and end portion 100f is a radially extending rib or stop portion 100h. In fact, the stop portion 100h may be defined by the sector of a circle whose axis coincides with the axis of the journal and end portions 100a, 100b and 100f. It will also be noted that a portion of a cap 11 may be machined in a flat surface 102 terminating in stop surfaces 103 and 104, the purposes of which will be more fully understood hereafter.

Figure 4:
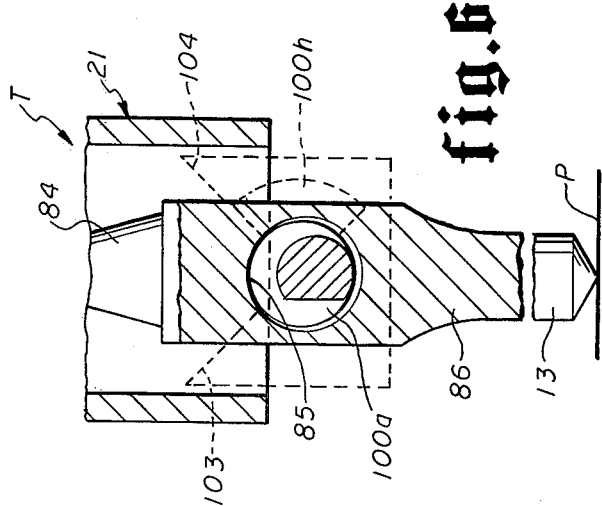
FIGS. 4, 5, and 6 are elevation views, similar to FIG. 3, but being partially in section to show movement of the operating cam of the present invention between no load, minor load and major load positions.
Figure 5:
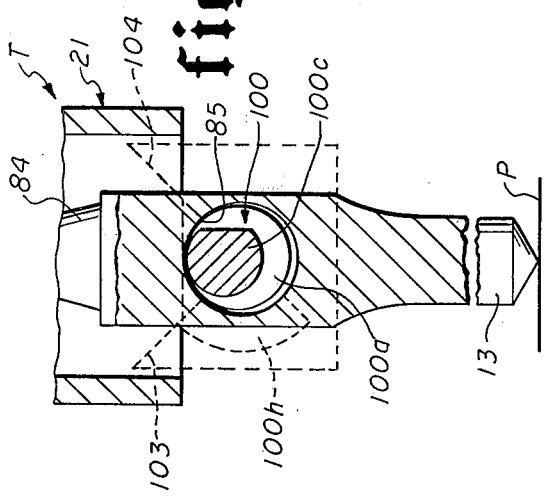
Figure 6:
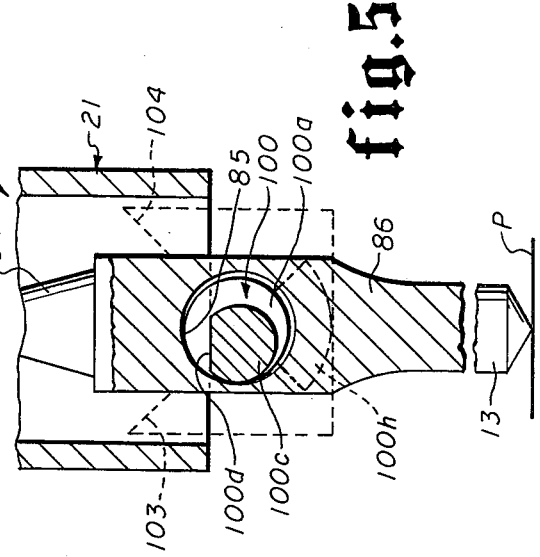

Referring now to FIGS. 4, 5, and 6, operation of the cam in no load, minor load and major load positions, respectively, will be described. In these drawings, portions of the tester T are shown in section so as to better understand the operation of the cam 100. In addition, the stop member 100h and the stop shoulders 103 and 104 are shown in dotted line to illustrate their relationship during these movements.

FIG. 4 shows the cam 100 in the no load position. In this position, the cam portion 100c is in its uppermost position engaging the upper confines of the hole 85 through enlarged portion 86 of stem 84 and also engaging the lower end of load cell 21. In this position, both the forces of the major load spring 82 and the minor load spring 88 (see FIG. 1) are prevented from being applied to the penetrator 13 through stem 84. Thus, no load is applied to the penetrator 13 for indentation of the plate P.

Next, by gripping the handle 101 (shown in FIG. 2) and rotating the cam member 100 ninety degrees in the counterclockwise direction, as viewed in FIGS. 4, 5 and 6, the cam 100 is rotated to the position of FIG. 5, the minor load position. In this position, the longitudinal flat surface 100d along one side of the smaller diameter cam portion 100c is facing upwardly for engagement with the lower end of load cell 21, again preventing the major load of the major load spring 82 (see FIGS. 1 and 2) from being applied to the penetrator 13. However, the cam portion 100c no longer engages the upper confines of the hole 85 through enlarged portion 86. This allows the force of the minor load spring 88 (see FIG. 1) to be applied to the penetrator 13. This minor load causes a slight indentation of plate P and a reading of the dial indicator 25 (FIG. 1) is taken at this point.

Next, the cam member 100 is rotated still further ninety degrees to the position shown in FIG. 6. In this position the smaller diameter cam portion 100c is at its lowermost position, no longer engaging either the upper confines of hole 85 or the lower end of load cell 21. Thus, the force of both the major load spring 82 and the minor load spring 88 (see FIG. 1) are applied to the penetrator 13. The major load indentation reading is then taken. The hardness of the material P is then determined from the difference in penetration between the minor load position of FIG. 5 and the major load position of FIG. 6.

It will be noted that in the no load position of FIG. 4, the radial rib stop member 100h is in engagement with the stop shoulder 103 of the closure cap 11. It will also be noted that in the major load position of FIG. 6, the radial rib stop member 100h engages the stop shoulder 104 of the cap 11. The stop members thus limit rotation of the cam member 100 between the no load and major load positions. These stop members are not in mutual engagement with corresponding stop shoulders in the minor load position of FIG. 5. However, due to the engagement of the flat surface 100d with the bottom of the load cell 21, the minor load position can be determined by feel on the operating handle 101.

Such a stop arrangement is much superior to the stop pin construction of the prior art (see 16f of FIG. 1). For one thing, the rib portion 100h provides greater strength and resistance against shearing than pin-type stop members of the prior art. In addition, the rib portion 100h is located at a greater diameter than is the stop pin of the prior art so that the torque applied thereto from the handle or operating end portion is less than that created in the prior art versions.

In addition, it will be noted that unlike the prior art version, the stop rib 100h is located directly adjacent to the larger diameter end portion 100f. When the stop members are engaged, torque is being applied to the larger diameter portion 100f and not to the smaller diameter portion 100c as in the prior art versions. Thus, breakage of the cam member 100 by twisting in two its weakest link, the smaller diameter cam portion 100c, is eliminated. In fact, there is no torque on the smaller diameter portion 100c. Furthermore, since there is no torque on the smaller diameter portion 100c, it cannot be distorted so as to result in inaccurate readings as in the prior art embodiment.

From the foregoing description, it is seen that the operating cam 100 of the present invention is much superior to the operating cam 16 of the prior art in both strength and accuracy. The use of such an operating cam should eliminate the breakage and consequential repair and lost time problems associated with designs of the prior art.

While a single embodiment of the invention has been described herein, many variations can be made without departing from the spirit of the invention. It is therefore intended that the scope of the invention be limited only by the claims which follow.

I claim:

1. An operating cam for use with a hardness tester of the type having a tubular housing in which is carried a load cell having major and minor load springs and to the lower end of which is attached a housing closure and a penetrator assembly which includes a reciprocating penetrator and a plunger rod engageable with said penetrator, said penetrator being movable between no load, minor load and major load positions, for measuring hardness properties of materials to be tested by said tester in response to loads applied by said load cell through said plunger rod, said operating cam being movable between no load, minor load and major load positions, in which no load, minor load and major load forces, respectively, of said load cell are applied to said penetrator through said plunger rod, said operating cam extending through a hole in said plunger rod perpendicular to the axis of said plunger rod, and rotatingly supported in first and second cylindrical holes through said housing closure on opposite sides of said plunger rod, said operating cam comprising:

first and second cylindrical journal portions for disposition within said first and second cylindrical holes, respectively;

a substantially cylindrical cam portion of smaller diameter between said journal portions and the axis of which is eccentric to the axis of said journal portions;

an end portion adjacent said second journal portion having a common axis with said journal portions and having means thereon for rotating said cam member about said common axis between said no load, minor load and major load positions; and cam stop means adjacent said end portion including at least one stop member projecting radially from one part of said end portion and engageable with corresponding stop means on said housing for limiting rotation of said operating cam between said no load and major load positions.

2. An operating cam as set forth in claim 1 including retainer means engageable with one end of said operating cam at said first journal portion to prevent displacement of said operating cam from said housing closure holes.

3. An operating cam as set forth in claim 1 in which said stop member is defined by the sector of a circle whose axis coincides with the axis of said journal and end portions.

4. An operating cam as set forth in claim 3 in which said housing stop means comprises first and second shoulders engageable by radial first and second sector edges of said stop member.

5. An operating cam as set forth in claim 1 in which the outer end of said end portion is provided with means for engagement by a handle member for said rotation of said operating cam.

6. An operating cam as set forth in claim 5 in which said end portion is cylindrical and of a diameter at least as great as the diameter of said journal portions.

7. An operating cam as set forth in claim 1 in which a flat surface is provided along one side of said cylindrical cam portion parallel to the axis thereof.

8. An operating cam as set forth in claim 7 in which a cylindrical surface of said cam portion is positioned against said load cell in said no load position, preventing both said minor and major load forces from being applied to said penetrator, said flat surface of said cam portion is positioned against said load cell in said minor load position, allowing only said minor load force to be applied to said penetrator, and no surface of said cam portion being positioned against said load cell in said major load position allowing said major load force to be applied to said penetrator.

9. An operating cam as set forth in claim 8 in which said operating cam stop means engages said corresponding housing stop means when said operating cam is in said no load and major load positions.

* * * * *